United States Patent [19]

Davidson et al.

[11] 4,340,569

[45] Jul. 20, 1982

[54] TREATMENT OF CARBONYLATION RESIDUES

[75] Inventors: Walter C. Davidson, Mahwah, N.J.; Richard V. Porcelli, Yonkers, N.Y.

[73] Assignee: The Halcon SD Group, Inc., New York, N.Y.

[21] Appl. No.: 241,180

[22] Filed: Mar. 6, 1981

[51] Int. Cl.³ .............................................. C01G 55/00
[52] U.S. Cl. .................................... 423/22; 252/413; 252/414; 252/415; 260/546; 260/549
[58] Field of Search ................. 423/22; 252/412–414, 252/415; 75/121

[56] References Cited

U.S. PATENT DOCUMENTS

| | | |
|---|---|---|
| 2,839,580 | 6/1958 | Hughes et al. |
| 2,880,241 | 3/1959 | Hughes . |
| 3,420,873 | 1/1969 | Olivier . |
| 3,437,431 | 4/1969 | Platz et al. ............................ 423/22 |
| 3,539,634 | 11/1970 | Olivier et al. . |
| 3,547,964 | 12/1970 | Olivier ............................ 260/429 R |
| 3,560,539 | 2/1971 | Booth . |
| 3,579,552 | 5/1971 | Craddock et al. . |
| 3,641,076 | 2/1972 | Booth ............................ 260/429 R |
| 3,716,626 | 2/1973 | Kniese et al. ........................ 423/418 |
| 3,755,393 | 8/1973 | Kniese et al. ........................ 252/412 |
| 3,821,311 | 6/1974 | Hughes et al. . |
| 3,857,895 | 12/1974 | Booth . |
| 3,899,442 | 8/1975 | Friedrich ............................ 252/416 |
| 3,901,822 | 8/1975 | Browning et al. .................. 252/414 |
| 3,920,449 | 11/1975 | Onoda et al. ........................ 252/414 |
| 3,978,148 | 8/1976 | Pertron ................................. 423/22 |
| 4,021,463 | 5/1977 | Kummer et al. ..................... 252/413 |
| 4,115,444 | 9/1978 | Rizkalla ................................ 260/549 |
| 4,164,481 | 8/1979 | Ma et al. .............................. 252/412 |
| 4,188,363 | 2/1980 | Fill et al. ............................... 423/22 |
| 4,251,458 | 2/1981 | Pugach ................................ 260/546 |

FOREIGN PATENT DOCUMENTS

| | | |
|---|---|---|
| 1468940 | 3/1977 | United Kingdom . |
| 1538782 | 1/1979 | United Kingdom . |
| 2038829A | 7/1980 | United Kingdom . |

Primary Examiner—Herbert T. Carter
Attorney, Agent, or Firm—William C. Long; Riggs T. Stewart; Harold N. Wells

[57] ABSTRACT

Residues are formed in the carbonylation of esters or ethers, particularly in the production of acetic anhydride or ethylidene diacetate. When such residues contain noble metal, typically rhodium, used as a catalyst, the noble metals must be recovered before the residues can be disposed of. The metal values are freed from the residues by treatment with amines, thereby enabling the rhodium to be extracted by subsequent contact with an aqueous halogen acid. The residues are pretreated with alkanols and concentrated by evaporation to improve the effect of such amine treatments.

16 Claims, No Drawings

TREATMENT OF CARBONYLATION RESIDUES

PRIOR ART

Complex catalysts employing Group VIII noble metals, particularly rhodium, are used for the homogenous catalysis of reactions in which carbon monoxide and hydrogen may be reacted with various organic molecules to produce compounds having a higher molecular weight. The reactions of particular interest with respect to the present invention are those generally designated as hydroformylation and carbonylation. Such reactions are shown in many patents, for example U.S. Pat. Nos. 3,579,552 and 4,115,444 and British Pat. Nos. 1,468,940 and 1,538,782. The noble metal catalysts are considered to be complexes which typically include carbon monoxide, promoting metals, and other non-metallic promoters, particularly phosphorus-containing ligands.

Reaction products must be separated from the homogenous catalyst. Typically, this is done by distilling the reactor effluent to separate the organic compounds and leaving behind the noble metal catalyst and other heavier materials which can then be recycled to the reaction vessel. The prior art discloses means by which the noble metal is recovered directly from reactor effluents for further use. However, in general the art indicates that heavy residues accumulate and must be purged from the reaction system. Such residues contain substantial amounts of noble metal which must be recovered in order for the process to be carried out economically. Since rhodium is the principal noble metal used, the discussion herein will refer for convenience specifically to rhodium, but it is to be understood that other noble metals are not excluded.

Rhodium has been recovered by many techniques, but at least three general approaches have been disclosed. First, the rhodium is recovered as the metal itself, which could require reformulation of the catalyst for further use. Second, the rhodium may be recovered on a solid material, which may serve as a catalyst support. Third, the rhodium is recovered in a form acceptable for returning to the reactor, with or without some additional processing to improve its catalytic properties.

Rhodium may be recovered as a metal by pyrolysis as shown in U.S. Pat. No. 3,920,449, which involves the high temperature decomposition of residues and rhodium-containing catalyst. The rhodium can then be reprocessed as required to provide catalyst or catalyst precursors for recycle to the reaction mixture.

The second recovery technique may be illustrated by U.S. Pat. No. 3,899,442 in which rhodium is deposited on a solid support in conjunction with pyrolysis of the residues. An alternative is shown in U.S. Pat. No. 3,978,148 in which rhodium is adsorbed on activated carbon, from which it could be recovered.

The third recovery technique is of particular interest with respect to the present invention, since it involves a recovery of rhodium by precipitation from solution in a form which is not necessarily metallic, but may be returned directly to the reaction vessel or pretreated before the recycling. Many methods of this sort have been disclosed in the prior art. Although the catalyst typically is soluble under reaction conditions, it may be possible to form insoluble compounds by the addition of water as shown in U.S. Pat. Nos. 2,839,580, 2,880,241, and 3,821,311. U.S. Pat. No. 3,887,489 shows the precipitation of rhodium-containing compounds by heating reaction residues for a sufficient period of time and temperature. Another technique shown in U.S. Pat. No. 3,560,359 is the use of hydrogen or hydrides to reduce carbonyl content of the tar to hydroxyl groups and thereby to release the rhodium complex which precipitates and can be recovered. The selective adsorption of the residues to separate them from the rhodium catalyst is in U.S. Pat. No. 3,539,634. The opposite approach, namely, the adsorption of rhodium on a solid adsorbent is disclosed in U.S. Pat. No. 3,716,626.

Particularly relevant to the present invention is prior art showing the extraction of rhodium from reaction residues with strong acids accompanied by water and often solvents. Typical disclosures are found in U.S. Pat. Nos. 3,420,873, 3,641,076, and 3,857,895. Related treatments with acids and peroxides are shown in U.S. Pat. Nos. 3,547,964 and 4,021,463.

In connection with the carbonylation process to be completely described both hereinafter and in U.S. Pat. Nos. 4,115,444 and 4,251,458 and British Pat. Nos. 1,468,940 and 1,538,782, it has been found that carbonylation reaction residues are not easily separated from the rhodium which they contain. Use of acid treatments typical of the prior art have been found to provide only incomplete recovery of the rhodium content. Since the remaining rhodium appears bound to the reaction residues, an improved method for completely recovering those rhodium values has been sought and is disclosed in commonly assigned applications. It has been found that pretreatment of such residues affects the ability to free the rhodium content as disclosed hereafter.

SUMMARY OF THE INVENTION

Residues created during carbonylation reactions, particularly the carbonylation of esters or ethers, especially carbonylation of methyl acetate or dimethyl ether to acetic anhydride or ethylidene diacetate, appear to bind Group VIII noble metals typically rhodium, and to be resistant to extraction by strong acids. When such residues are treated with amines, preferably primary aliphatic amines and/or hydrazine, the rhodium can then be extracted by subsequent contact with a halogen acid. Preferred are compounds containing 0-4 carbon atoms, especially n-propyl amine and hydrazine.

The ability of the amines to free rhodium from the residues is affected by the manner in which the volatile components are removed from the residues. According to the method of the invention, residues are treated with alkanols, preferably methanol, and concentrated by heating at relatively low temperatures, preferably no higher than 25° C. under a suitable vacuum, typically about 25 mm Hg absolute, until substantially all of the volatile components have been removed.

DESCRIPTION OF THE PREFERRED EMBODIMENTS

The recovery of Group VIII noble metals, especially rhodium, from carbonylation and hydroformulation reaction residues has been of considerable interest to those skilled in the art. Of particular concern to the present inventors is the recovery of Group VIII noble metals, particularly rhodium, from catalysts used in the carbonylation of a carboxylate ester or an alkyl ether to an anhydride, especially the carbonylation of methyl acetate or dimethyl ether to acetic anhydride. In another aspect, the invention relates to recovery of similar rhodium catalysts used for the carbonylation in the presence of hydrogen of methyl acetate or dimethyl ether to ethylidene diacetate. These processes have been described in depth in U.S. Pat. Nos. 4,115,444 and 4,251,458 and in British Pat. Nos. 1,468,940 and 1,538,782 and they are summarized below. A related process is shown in British publication GB Pat. No. 2,038,829A in which methyl acetate is reacted with carbon monoxide and hydrogen to produce acetaldehyde in the presence of a palladium catalyst. The processes are important since they produce chemicals of value, both for direct use and as intermediates. However, the recovery of Group VIII noble metals according to the present invention is not considered to be limited only to these particular carbonylation processes.

Preparation of Carboxylic Acid Anhydrides

The process for the preparation of an anhydride of a monocarboxylic acid in general comprises carbonylation of a carboxylate ester (RCOOR) or an ether (ROR) in the presence of a Group VIII noble metal catalyst and a halogen, the R's may be the same or different and each R is a monovalent hydrocarbon radical or a substituted monovalent hydrocarbon radical wherein any substituent is inert.

Of particular interest, acetic anhydride can be effectively prepared by carbonylating methyl acetate or dimethyl ether under a moderate CO partial pressures in the presence of a Group VIII noble metal catalyst and iodides or bromides. Various metallic and non-metallic promoters may be present. Other alkanoic anhydrides, such as propionic anhydride, butyric anhydrides and valeric anhydrides, can be produced by carbonylating the corresponding lower alkyl alkanoate or a lower alkyl ether.

Preparation of Ethylidene Diacetate

The preparation of ethylidene diacetate comprises contacting (a) methyl acetate or dimethyl ether, (b) carbon monoxide, and (c) hydrogen with a source of halide comprising a bromide and/or an iodide, within a reaction zone under substantially anhydrous conditions in the presence of a Group VIII noble metal catalyst. Again, various metallic and non-metallic promoters may be present.

The overall reaction can be expressed by the following chemical equation:

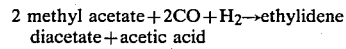
2 methyl acetate + 2CO + $H_2$ → ethylidene diacetate + acetic acid

When dimethyl ether is used as the reactant in lieu of methyl acetate, the overall reaction is can be expressed by the following chemical equation:

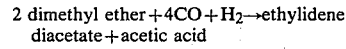
2 dimethyl ether + 4CO + $H_2$ → ethylidene diacetate + acetic acid

When using dimethyl ether as the organic raw material it is believed that the initial step involved is the carbonylation of the ether to produce methyl acetate. This may be done in a separate reaction zone. However, the use of a separate reaction zone is not necessary because the conversion of dimethyl ether to methyl acetate can be carried out concurrently with and in the same reaction zone as that in which the ethylidene diacetate is formed.

Reaction Conditions

In carrying out the reactions, a wide range of temperatures, e.g. 20° to 500° C., are suitable but temperatures of 100° to 300° C. are typically employed and the more preferred temperatures generally lie in the range of 125° to 250° C. The reaction is carried out under superatmospheric pressure and employing a carbon monoxide partial pressure which is preferably 0.35 to 140.6 kg/cm$^2$, and most preferably 1.76 to 70.3 kg/cm$^2$, although carbon monoxide partial pressures of 0.007 to 1055 kg/cm$^2$ can also be employed. The total pressure is preferably that required to maintain the liquid phase.

The Group VIII noble metal catalyst, i.e., iridium, osmium, platinum, palladium, rhodium or ruthenium, can be supplied in the zero valent state or in any higher valent form. For example, the catalyst to be added may be the metal itself in finely divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Similarly complexes of the metals can be employed for example the metal carbonyls, such as iridium carbonyls and rhodium carbonyls, or as other complexes such as the carbonyl halides, e.g., iridium tri-carbonyl chloride

[Ir(CO)$_3$Cl]$_2$ or the acetylacetonates, e.g. rhodium acetylacetonate

Rh(C$_5$H$_7$O$_2$)$_3$.

Preformed ligand-like complexes can also be employed, such as dichloro bis-(triphenylphosphine) palladium, dichloro bis-(triphenylphosphine) rhodium, and trichloro tris-pyridene rhodium. Other forms in which the catalyst can be added to the system include, aside from those already specifically listed, rhodium oxide (Rh$_2$O$_3$), tetrarhodium dodecacarbonyl, dirhodium octacarbonyl, hexarhodium hexadecacarbonyl (Rh$_6$(CO)$_{16}$), rhodium (II) formate, rhodium (II) acetate, rhodium (II) propionate, rhodium (II) butyrate, rhodium (II) valerate, rhodium (III) naphthenate, rhodium dicarbonyl acetylacetonate, rhodium trihydroxide, irdenylrhodium dicarbonyl, rhodium, dicarbonyl (1-phenylbutane-1,3-dione), tris(hexane-2,4-dione) rhodium (III), tris(heptane-2,4-dione) rhodium (III), tris(1-phenylbutane-1,3-dione) rhodium (III), tris(3-methylpentane-2,4-dione) rhodium (III), and tris(1-cyclohexylbutane-1,3-dione) rhodium (III).

The noble metal catalyst can be employed in forms initially or eventually soluble in the liquid phase reaction medium to provide a homogenous catalyst system. Alternatively, insoluble (or only partially soluble) forms, providing a heterogeneous catalyst system, can be employed. Amounts of carbonylation catalyst (calculated as contained noble metal based upon the total quantity of liquid phase reaction medium) of as little as about 1×10$^{-4}$ wt. % (1 ppm) are effective, although normally amounts of at least 10 ppm, desirably at least 25 ppm, and preferably at least 50 ppm would be employed. An optimum balancing of reaction rate and economic criteria would normally suggest the use of amounts of contained noble metal carbonylation catalyst based upon the total weight of liquid phase reaction medium between about 10 and about 50,000 ppm, desirably between about 100 and 25,000 ppm, and preferably between about 500 to 10,000 ppm.

Activity of the Group VIII noble metal catalysts described above can be significantly improved, particularly with respect to reaction rate and product concentration, by the concurrent use of a promoter. Effective promoters include the elements having atomic weights greater than 5 of Groups IA, IIA, IIIA, IVB, VB, VIB, the non-noble metals of Groups VIII and the metals of the lanthanide and actinide groups of the Periodic Table. Preferred inorganic promoters include the metals of Groups VIB and the non-noble metals of Group VIII, especially chromium, iron, cobalt, and nickel and most preferably chromium. Particularly preferred are the lower atomic weight metals of each of these groups, i.e. those having atomic weights lower than 100, and especially preferred are the metals of Groups IA, IIA and IIIA. In general, the most suitable elements are lithium, magnesium, calcium, titanium, chromium, iron, nickel and aluminum. The promoters may be used in their elemental form e.g. as finely-divided or powdered metals, or they may be employed as compounds of various types, both organic and inorganic, which are effective to introduce the element into the reaction system, such as oxides, hydroxides, halides, e.g. bromides and iodides, oxyhalides, hydrides, alkoxides, and the like. Especially preferred organic compounds are the salts of organic monocarboxylic acids e.g. alkanoates such as acetates, butyrates, decanoates and laurates, benzoates, and the like. Other compounds include the metal alkyls, carbonyl compounds as well as chelates, association compounds and enol salts. Particularly preferred are the elemental forms, compounds which are bromides or iodides, and organic salts e.g. salts of the mono-carboxylic acid corresponding to the anhydride being produced. Mixtures of promoters can be used, if desired, especially mixtures of elements from different Groups of the Periodic Table.

The quantity of the promoter can vary widely, but preferably it is used in the amount of 0.001 mol to 100 mols per mol of Group VIII noble metal catalyst, most preferably 0.001 to 10 mols per mol of catalyst.

In the separation of the products from the reaction mixtures, the promoter generally remains with the Group VIII noble metal catalyst, i.e. as one of the least volatile components, and is suitably recycled or otherwise handled along with the catalyst.

Organic promoters capable of forming a coordination compound with the Group VIII noble metal catalyst are beneficial, particularly organic non-hydrocarbon materials containing within their molecular structure one or more electron rich atoms having one or more pairs of electrons available for formation of coordinate bonds with the noble metal catalyst. Most such organic promoters can be characterized as Lewis bases for the particular anhydrous reaction system involved.

Suitable organic promoters are non-hydrocarbon materials capable of forming a coordination compound with the Group VIII noble metal catalyst,, containing within their molecular structure one or more pairs of electrons available for formation of coordinate bonds with the noble metal catalyst. Such promoters can be introduced concurrently with the reactants to the reaction zone or can be incorporated together with the Group VIII noble metal by formation of ligand complexes with the noble metal prior to introduction of the noble metal-ligand complex to the reaction zone.

Suitable organic promoters are organo-phosphine, organo-arsine, organo-stibine, organo-nitrogen, and organo-oxygen containing compounds. Organo-phosphine and organo-nitrogen promoters are preferred classes.

Suitable oxygen-containing compounds capable of functioning as organic promoters in this system are those containing functional groups such as the phenolic hydroxyl, carboxyl, carbonyloxy and carbonyl groups. Suitable organo-nitrogen containing compounds are those containing amino, imino and nitrilo groups. Materials containing both oxygen and nitrogen atoms can be used.

Illustrative organic promoters of the types mentioned above may be found in British Pat. No. 1,538,782.

The quality of organic promoter employed is related to the quantity of noble metal catalyst within the reaction zone. Normally the quantity is such that at least 0.1, desirably at least 0.2, and preferably at least 0.3 mol of promoter compound per mol of noble metal is present in the reaction zone. Preferably less than 100 mols of promoter per mol of noble metal catalyst would be used.

Carbon monoxide and hydrogen are preferably employed in substantially pure form, as available commercially. However, inert diluents such as carbon dioxide, nitrogen, methane, and/or inert gases (e.g., helium, argon, neon, etc.) can be present.

All reactants should be substantially free from water since, in this fashion, the maintenance of a substantially anhydrous condition within the reaction zone is facilitated. The presence of minor amounts of water, however, such as may be found in these commercially available reactants, is permissible. Normally, however, the presence of more than 5 mol % of water in any one or more of the reactants should be avoided, the presence of less than 3 mol % of water is desired, and the presence of less than 1.0 mol % of water is preferred. More important, however, than the amount of water in feed or recycle streams introduced to the reaction zone is the concentration of free water plus alcoholic hydroxyl groups (which react in situ to form water) present within the reaction zone. In practice, the molar ratio of (a) water plus the molar equivalents of alcoholic hydroxyl groups to (b) the number of mols of dimethyl ether and/or methyl acetate within the reaction zone is the most convenient method for defining this concentration. On this basis, this ratio preferably should not exceed 0.1:1. Still lower values for this ratio are advantageous, with optimal results being obtained with values for this ratio ranging from zero to 0.05:1.

Solvents or diluents can be employed, preferably materials which are indigenous to the reaction system and/or co-products commonly found in the reaction system. Excess dimethyl ether and/or methyl acetate are the preferred reaction diluents, with acetic acid being the preferred alternate. It is also practicable to employ organic solvents or diluents which are inert in the environment of the process. The most suitable inert solvents or diluents are hydrocarbons free from olefinic unsaturation, typically the paraffinic, cycloparaffinic, and aromatic hydrocarbons such as octane, cyclododecane, benzene, toluene, and the xylenes. Other suitable solvents include chloroform, carbon tetrachloride, and acetone.

The reactions require the presence of a halide, which would be a component of the liquid phase reaction medium. Suitable halides are either bromide or iodide or mixtures thereof, iodide being preferred. The halide would usually be present largely in the form of methyl halide, acetyl halide, hydrogen halide, or mixtures of the foregoing species, and could be introduced to the liquid phase reaction medium as such. However, these materials may be formed in situ, by using inorganic halide materials, e.g., salts such as the alkali metal and alkaline earth metal salts, as well as elemental iodine and bromine. In continuous operation, wherein reaction by-products are separated and recycled to the reaction medium, organic halides such as methyl halide will be present as components of the liquid phase reaction medium and can be recovered and recycled to the reaction zone as such; thus, only a small quantity of make-up halide need be supplied to compensate for such losses in recovery as may be encountered.

The amount of halide that should be present in the liquid phase reaction medium is related to the amount of ether and/or ester reactant introduced to the reaction zone, but otherwise can vary over a wide range. Typically, 0.5 to 1,000 mols of ester and/or ether per equivalent of halide, desirably 1 to 300 mols per equivalent, and preferably 2 to 100 mols per equivalent are used. In general, higher proportions of halide to ether and/or ester reactant tend to increase reaction rate.

It has been found that molar ratios of carbon monoxide to hydrogen, broadly within the range of 1:100 to 100:1, desirably within the range of 50:1 to 1:50, and preferably within the range of 10:1 to 1:10 can be employed. Best results are obtained with carbon monoxide-hydrogen mixtures which approach the stoichiometric ratios of carbon monoxide to hydrogen. Molar ratios of carbon monoxide to hydrogen within the range of 0.5:1 to 5:1 are thus especially preferred.

Recovery of Noble Metals

The invention broadly relates to the recovery of Group VIII noble metals, typically rhodium, which appear to be bound to heavy high-boiling residues produced by carbonylation reactions, with or without hydrogen being present. Residues from such reactions are complex and have not been definitely analyzed. Generally, they are known to contain high molecular weight compounds with organic carbonyl and acetate functions. They contain typically about 0–4 percent by weight rhodium after the volatile constituents have been removed. It is characteristic of such residues that they cannot be freed of all the rhodium (or other noble metal) by extraction with halogen acids, such as disclosed in the prior art.

The following example will illustrate a carbonylation process which produces heavy residues containing substantial amounts of rhodium.

EXAMPLE I

A one liter autoclave was operated continuously to produce acetic anhydride by the carbonylation of methyl acetate. The reactants, i.e. methyl acetate, methyl iodide, carbon monoxide and hydrogen are added continuously, while the product acetic anhydride is removed as a vapor, condensed, and separated from the non-condensibles, which are returned to the reactor. The reaction is catalyzed by the mixture of rhodium trichloride trihydrate, and lithium iodide, which are added to the initial charge placed in the autoclave in amounts sufficient to provide about 0.01 mol Rh/liter of liquid in the vessel and 60 mol Li/mol Rh. The reaction is operated at about 190° C., 50 kg/cm$^2$ absolute, with partial pressures of about 40 kg/cm$^2$ CO and about 2.5 kg/cm$^2$ H$_2$. The residues are withdrawn at a rate sufficient to maintain a desired concentration in the autoclave and treated to recover the rhodium values. The reaction mixture after being freed of a portion of its volatile components contains about 6 wt % methyl iodide, 10 wt % methyl acetate, 50 wt % acetic anhydride, a small amount of ethylidene diacetate, 15–20 wt % acetic acid, with about 15 wt % heavy residues containing catalyst.

It has been found that treatment of heavy residues with halogen acids, disclosed in some of the prior art to be useful for extracting rhodium, is not adequate for commercial application since the high cost of rhodium makes nearly complete recovery essential. As will be seen in related commonly assigned applications, (Ser. Nos. 241,193 and 241,181) acid treatment alone is insufficient with heavy residues produced by the carbonylation processes of which Example I is representative.

The reagents which may be used to free rhodium (or other noble metals) from carbonylation residues are generally classified as amines, and particularly the primary aliphatic amines, especially n-propylamine which has physical characteristics suitable for treating the residues. For purposes of the invention, primary aliphatic amines are considered to include any reagent molecule with that functionality, regardless of other functions also present in the molecule, including examples such as 1,2 ethane diamine, 2 hydroxy ethylamine, 2 phenethyl amine, 2 chloro ethylamine, 1,6 hexane diamine, and 4 amino-1-butene. Also, hydrazine is preferred. Although it is not normally considered an amine, hydrazine has the characteristic properties of an amine and for purposes of this invention is to classified.

The contacting of the reagent with the carbonylation residue is carried out by removing as much of the carbonylation reaction mixture as possible to leave concentrated residues, then mixing the residue with one or more of the selected treating agents, at a temperature in the range of 20°–200° C., a pressure typically about one atmosphere for at least about one-half hour. Preferably, the amount of treating reagent(s) used will be at least one mol for each mol of carbonyl in the residue.

After the residue has been treated, it is contacted with a halogen acid, such as HCl, HI, or HBr. The acid may be added in various forms; typically an aqueous solution of about 10 wt % HCl or HI would be used. Generally, the acid will be introduced to the treated residue along with a solvent which can dissolve the residue and separate it from the aqueous layer which forms and which contains the extracted noble metal. While methylene chloride is used in the following examples, other solvents could be used such as the indigenous compounds methyl iodide and methyl acetate (although others could be used). The extraction may be carried out at room temperature, until the extraction is complete. Thereafter, the mixture is separated, with the residue being removed in the solvent for disposal and the aqueous layer processed to recover the noble metal content, reprocessed to form the catalyst, or recycled directly to the carbonylation reaction.

EXAMPLE II

Comparative Example

Two samples (A & B) of the residue withdrawn in Example I are held at temperatures of up to 150° C. and about 760 mm Hg absolute pressure (Sample A) and at 50° C. and 0-5 mm Hg absolute pressure (Sample B) for about 2 hours to evaporate volatile components and to leave behind only the heavy residues. The reduced residue contains about 1 wgt % rhodium as measured by atomic absorption spectroscopy. It is intimately mixed with 10 ml of a 3 N solution of HCl and 5 ml of methylene chloride at room temperature which extracts as much rhodium as possible. After mixing is stopped, two layers form, a methylene chloride layer containing the residue and an acid layer. No rhodium was removed by acid extraction in Sample A, but 32% of the rhodium was extracted in Sample B. The remainder of the rhodium is considered bound to the residue.

Since only part of the rhodium content is extracted by the acid, the remainder of must be recovered if intolerable losses of rhodium are to be avoided. This may be accomplished by further treating the already acid-extracted residues with reagents to free free the rhodium from the residues, permitting a second acid extraction to successfully separate the rhodium values.

The two samples of acid extracted residues are treated with a large excess of various reagents and then subjected to a second acid extraction. About 40-60 mg of the acid-treated residues in each sample is heated to about 110° C. in the presence of the reagent being tested for a period of 1-24 hours. Then, about 1 ml of 36 wt % aqueous HCl is added plus 3 ml of 3 N HCl, along with 3 ml of methylene chloride. After mixing, the acid and methylene chloride layers are permitted to separate and the acid layer is removed. Another 3 ml of 3 N HCl is added to repeat the extraction step. After separating the second acid layer, the extraction is repeated for a third time by adding another 3 ml of 3 N HCl. The acid layers from the three extractions are mixed and analyzed for rhodium. The results of a series of experiments carried out as described are reported in the following table.

TABLE 1

| Treating Agent | | % bound Rhodium Extracted | |
|---|---|---|---|
| | | Sample A | Sample B |
| 1 ml | n-butylamine | 1.9 | 21.4 |
| ½ ml | aniline | 1.0 | 8.6 |
| ½ ml | 1-propylamine | <1 | 72.3 |
| 42 mg | hydroxyl amine hydrochloride + 1 ml methylene chloride | 2.7 | 13.8 |
| 33 mg | hydroxyl amine hydrochloride + 1 ml n-butyl amine | 3.1 | 48.2 |
| — | 2,4 dinitrophenyl hydrazine + ½ ml methylene chloride | 2.4 | 5.7 |
| 0.2 ml | hydrazine monohydrate + 1 ml methylene chloride | 2.7 | 78 |
| 0.4 ml | phenyl hydrazine + 1 ml methylene chloride | <2.7 | <6.6 |

As the data in Table 1 shows, the vaporation of volatile materials at the higher temperatures of Sample A causes the rhodium content to be much less easily extracted by an aqueous halogen acid, even after treatment with an amine or hydrazine.

It has been discovered that preparation of the residues by contacting with an alkanol, preferably methanol, followed by evaporation at low temperatures, preferably not above about 25° C. An appropriate vacuum would be used, typically between 1 and 10 mm Hg absolute. The benefits of this preparation technique will be seen in the following example.

EXAMPLE III

A 41.5 gm portion of the residue of Example I is combined with 100 gms of methanol and shaken overnight. The mixture is then evaporated in a Buchi Rotavapor R rotary evaporator at room temperature (about 25° C.) under a vacuum of about 35 mm Hg absolute overnight to evaporate volatile compounds. The reduced material is 24% by weight of the original sample and contains about 0.34 wt% rhodium, as measured by atomic absorption spectroscopy. A 52.2 mg portion of the solids is treated with 0.5 ml of n-propyl amine at 100° C. for one hour. Then 1 ml of 35 wt % aqueous HCl and 4 ml of methylene chloride are added and the mixture extracted sequentially with three separate 3 ml portions of 3 N HCl, as in the previous examples. Analysis of the combined acid layers indicates that 96% of the rhodium had been extracted.

As shown in Example III and the Comparative Example II, the method of removing the volatile materials from carbonylation residues affects the ability of the amine (or hydrazine) treatment to free rhodium from the residues, permitting its subsequent extraction by an aqueous halogen acid. In the process of the invention, the carbonylation residue is contacted with at least one mol of an alkanol, preferably methanol, for each equivalent of acid ester and anhydride present in the heavy residue for a sufficient period of time, at least about one hour, and then the mixture is vaporized at a low temperature, preferably no higher than 25° C., and under a suitable vacuum, typically in the range of 1-40 mm Hg absolute. The concentrated residues are then especially susceptable to treatment and extraction, permitting substantially complete recovery of the rhodium content.

What is claimed is:

1. In a process for recovering Group VIII noble metals bound to residues of noble metal catalyzed carbonylation reactions comprising separating said residues, vaporizing the volatile components therefrom to produce a reduced residue, treating the reduced residues with an amine, and extracting said noble metals from said treated reduced residue with an aqueous halogen acid, the improvement comprising treating said residues with an alkanol or mixture thereof and thereafter vaporizing the volatile components at low temperatures and a suitable vacuum, thereby improving the subsequent recovery of said noble metals.

2. The process of claim 1 wherein said alkanol is methanol.

3. The process of claim 1 wherein said volatile components are removed at a temperature no higher than about 25° C.

4. The process of claim 1 wherein said vacuum is in the range of 1-40 mm Hg absolute.

5. The process of claim 1 wherein said alkanol is employed in at least one mol for every equivalent of acid ester and anhydride present in the residues.

6. The process of claim 1 wherein said carbonylation reaction is the carbonylation of methyl acetate or dimethyl ether to acetic anhydride.

7. The process of claim 1 wherein said carbonylation reaction is the carbonylation in the presence of hydrogen of methyl acetate or dimethyl ether to ethylidene diacetate.

8. The process for recovering Group VIII noble metals bound to residues of noble metal catalyzed carbonylation reactions comprising:

(a) separating said residues from the carbonylation reaction mixture;

(b) treating said separated residue of (a) with an alkanol or mixture thereof;

(c) vaporizing the volatile components of said treated residues of (b) at low temperatures and under a sufficient vacuum and recovering a reduced fraction therefrom;

(d) treating said reduced fraction of (c) with a reagent comprising an amine in an amount sufficient to free said noble metals;

(e) extracting said treated solid fraction of (d) with an aqueous halogen acid, thereby recovering the noble metals therefrom.

9. The process of claim 8 wherein said alkanol is methanol.

10. The process of claim 8 wherein said volatile components are removed at a temperature no higher than about 25° C.

11. The process of claim 8 wherein said vacuum is in the range of 1-40 mm Hg absolute.

12. The process of claim 8 wherein said alkanol is employed in at least one mol for every equivalent of acid ester and anhydride present in the residues.

13. The process of claim 8 wherein said carbonylation reaction is the carbonylation of methyl acetate or dimethyl ether to acetic anhydride.

14. The process of claim 8 wherein said carbonylation reaction is the carbonylation in the presence of hydrogen of methyl acetate or dimethyl ether to ethylidene diacetate.

15. The process of claim 8 wherein said amine reagent is at least one member of the group consisting of primary aliphatic amines and hydrazine.

16. The process of claim 8 wherein said Group VIII noble metal is rhodium.

* * * * *

UNITED STATES PATENT AND TRADEMARK OFFICE
CERTIFICATE OF CORRECTION

PATENT NO. : 4,340,569
DATED : July 20, 1982
INVENTOR(S) : Walter C. Davidson and Richard V. Porcelli It is certified that error appears in the above-identified patent and that said Letters Patent are hereby corrected as shown below:

Column 3, line 6 -- delete "Pat. No.";

Column 5, line 41 -- change "0.001" to -- 0.0001 --.

Signed and Sealed this

Twenty-first Day of September 1982

[SEAL]

Attest:

GERALD J. MOSSINGHOFF

Attesting Officer     Commissioner of Patents and Trademarks